(12) United States Patent
Michelson

(10) Patent No.: US 7,066,961 B2
(45) Date of Patent: *Jun. 27, 2006

(54) SPINAL IMPLANT

(76) Inventor: Gary Karlin Michelson, 438 Sherman Canal, Venice, CA (US) 90291

( * ) Notice: Subject to any disclaimer, the term of this patent is extended or adjusted under 35 U.S.C. 154(b) by 0 days.

This patent is subject to a terminal disclaimer.

(21) Appl. No.: 10/292,539

(22) Filed: Nov. 12, 2002

(65) Prior Publication Data

US 2003/0149482 A1 Aug. 7, 2003

Related U.S. Application Data

(63) Continuation of application No. 09/580,768, filed on May 30, 2000, now Pat. No. 6,478,823, which is a continuation of application No. 29/056,996, filed on Jul. 15, 1996, now Pat. No. Des. 425,989, which is a continuation of application No. 29/023,922, filed on Jun. 3, 1994, now abandoned, which is a continuation of application No. 08/052,211, filed on Apr. 22, 1993, now abandoned, which is a continuation of application No. 07/546,849, filed on Jul. 2, 1990, now abandoned, which is a continuation of application No. 07/212,480, filed on Jun. 28, 1988, now abandoned.

(51) Int. Cl.
*A61F 2/44* (2006.01)

(52) U.S. Cl. ................... 623/17.16; 623/17.11

(58) Field of Classification Search ... 623/16.11–17.16
See application file for complete search history.

(56) References Cited

U.S. PATENT DOCUMENTS

| | | | |
|---|---|---|---|
| 3,298,372 A | 1/1967 | Feingberg | |
| 3,848,601 A | 11/1974 | Ma et al. | |
| 3,867,728 A | 2/1975 | Stubstad et al. | |
| 3,875,595 A | 4/1975 | Froning | |
| 3,948,262 A | 4/1976 | Zaffaroni | |
| D245,259 S | 8/1977 | Shen | |
| 4,309,777 A | 1/1982 | Patil | |
| 4,349,921 A | 9/1982 | Kuntz | |
| 4,401,112 A | 8/1983 | Rezaian | |
| 4,501,269 A | 2/1985 | Bagby | |
| 4,507,115 A | 3/1985 | Kambara et al. | |
| 4,542,539 A | 9/1985 | Rowe, Jr. et al. | |
| 4,545,374 A | 10/1985 | Jacobson | |
| 4,554,914 A | 11/1985 | Kapp et al. | |
| 4,599,086 A | 7/1986 | Doty | |
| 4,714,469 A | 12/1987 | Kenna | |
| 4,721,103 A | 1/1988 | Freedland | |
| 4,743,256 A | 5/1988 | Brantigan | |
| 4,759,766 A | 7/1988 | Buettner-Janz et al. | |
| 4,759,769 A | 7/1988 | Hedman et al. | |
| 4,763,644 A | 8/1988 | Webb | |
| 4,820,305 A | 4/1989 | Harms et al. | |

(Continued)

FOREIGN PATENT DOCUMENTS

DE     29 10 627     9/1980

(Continued)

OTHER PUBLICATIONS

*Anthrodesis by the Distraction-Compression Method Using a Stainless Steel Implant;* Bagby, M.D.; North American Spine Society, Jun. 1987.

(Continued)

*Primary Examiner*—Thomas Barrett
(74) *Attorney, Agent, or Firm*—Martin & Ferraro, LLP

(57) ABSTRACT

A spinal implant is disclosed which when placed within the spinal disc space stabilizes the spinal segment.

133 Claims, 13 Drawing Sheets

U.S. PATENT DOCUMENTS

| | | |
|---|---|---|
| 4,834,757 A | 5/1989 | Brantigan |
| 4,863,476 A | 9/1989 | Shepperd |
| 4,863,477 A | 9/1989 | Monson |
| 4,865,603 A | 9/1989 | Noiles |
| 4,877,020 A | 10/1989 | Vich |
| 4,878,915 A | 11/1989 | Brantigan |
| 4,904,261 A | 2/1990 | Dove et al. |
| 4,911,718 A | 3/1990 | Lee et al. |
| 4,955,908 A | 9/1990 | Frey et al. |
| 5,522,899 A | 6/1996 | Michelson |
| 5,609,635 A | 3/1997 | Michelson |

FOREIGN PATENT DOCUMENTS

| | | | |
|---|---|---|---|
| DE | 36 08 163 A1 | 9/1987 | |
| EP | 0 179 695 | 9/1985 | |
| EP | 0 260 044 | 8/1987 | |
| JP | 60-31706 | 11/1979 | |
| JP | 57-29348 | 2/1982 | |
| JP | 60-43984 | 10/1985 | |
| JP | 61-122859 | 6/1986 | |
| JP | 62-155846 | 7/1987 | |
| SU | 1107854 | 8/1984 | 623/17 |

OTHER PUBLICATIONS

*A Dowell Inserter for Anterior Cervical Interbody Fusion;* Brand, L., et al.; J. Neurosurg. 61:793-794 (Oct. 1984).

*Outline of Orthopaedics;* Eleventh Edition; Adams, Hamblen; Trunk and Spine, p. 194.

*Spinal Fusion Science and Technique;* Cotler and Cotler; The Biology of Spinal Fusion, Muscheler, Lane and Dawson, pp. 9-13.

*The Spine;* Third Edition; Herkowitz, Garfin, Balderston, Bismont, Bell Wiesel, Spinal Fusion—Chapter 44, p. 1739; Principles of Bone Fusion, Lane, Muschler.

Tech. Mitt. Krupp, Nickel-Titanium Spacers For Partial Stiffening Of The Spinal Column—Problems Involved, Manufacture, Pretesting, And Clinichal Use; vol. 42 (1984), No. 1, pp. 24-38; including translation pp. 5-27.

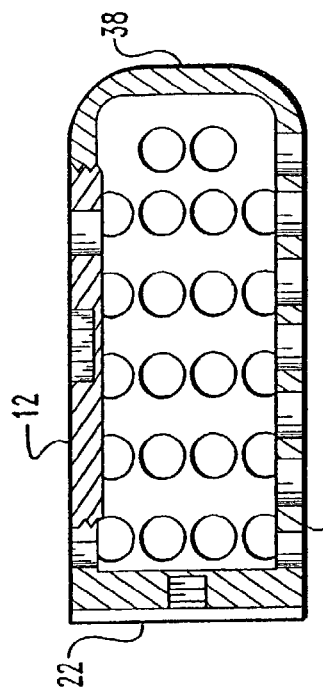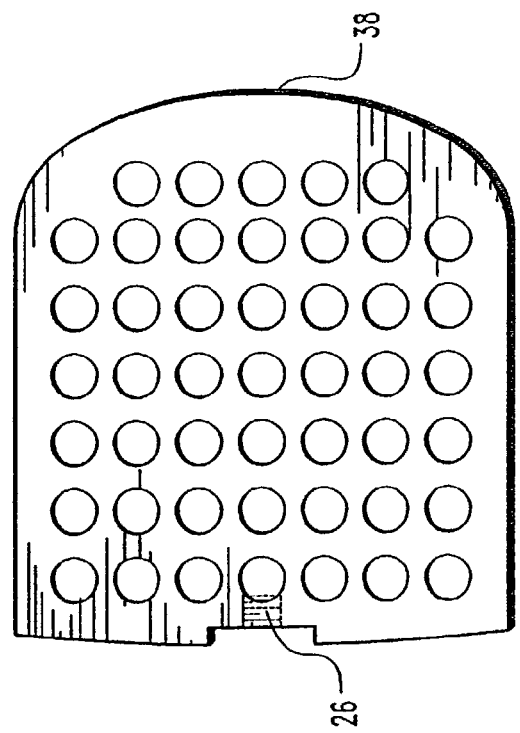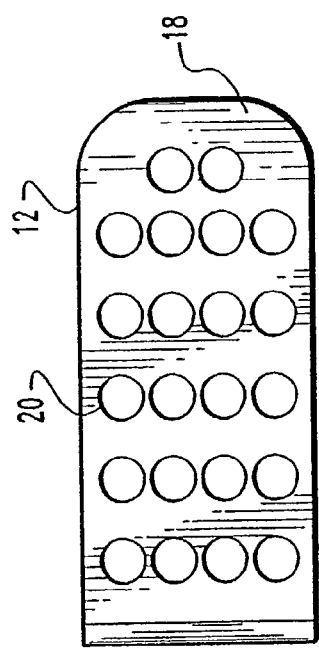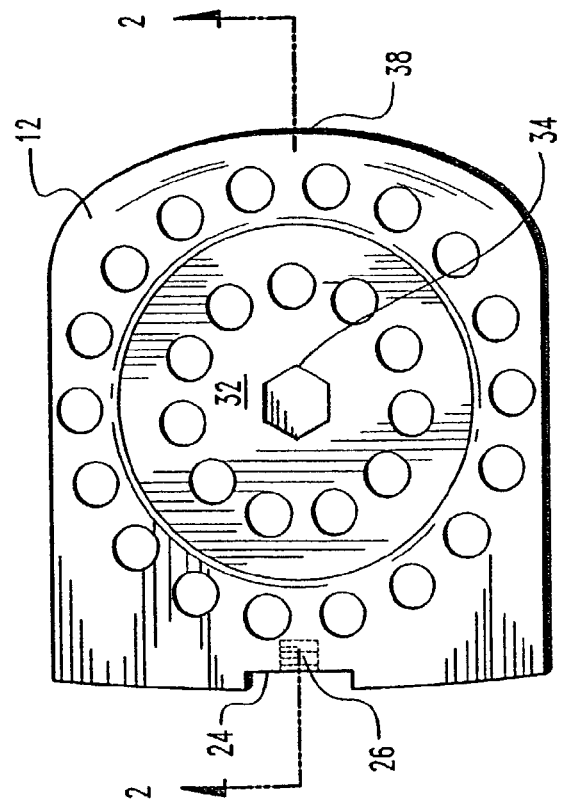

SPINAL IMPLANT

This is a continuation application Ser. No. 09/580,768, filed May 30, 2000, now U.S. Pat. No. 6,478,823; which is a continuation-in-part of application Ser. No. 29/056,996, filed Jul. 15, 1996, now U.S. Pat. No. D425,989; which is a continuation of application Ser. No. 29/023,922, filed Jun. 3, 1994, now abandoned; which is a continuation of application Ser. No. 08/052,211, filed on Apr. 22, 1993, now abandoned; which is a continuation of application Ser. No. 07/546,849, filed Jul. 2, 1990, now abandoned; which is a continuation of application Ser. No. 07/212,480, filed Jun. 28, 1988, now abandoned; all of which are incorporated herein by reference.

BACKGROUND

The present invention relates to an artificial fusion implant to be placed into the intervertebral space left after the removal of a damaged spinal disc.

The purpose of the present invention is to provide an implant to be placed within the intervertebral disc space and provide for the permanent elimination of all motion at that location. To do so, the device is space occupying within the disc space, rigid, self-stabilizing to resist dislodgement, stabilizing to the adjacent spinal vertebrae to eliminate local motion, and able to intrinsically participate in a vertebra to vertebra bony fusion so as to assure the permanency of the result.

At present, following the removal of a damaged disc, either bone or nothing is placed into the space left. If nothing is placed in the space the space may collapse which may result in damage to the nerves; or the space may fill with scar tissue and eventually lead to a reherniation. The use of bone is less than optimal in that the bone obtained from the patient requires additional surgery and is of limited availability in its most useful form and if obtained elsewhere, lacks living bone cells, carries a significant risk of infection, and is also limited in supply as it is usually obtained from young accident victims. Furthermore, regardless of the source of the bone, it is only marginal structurally and lacks a means to either stabilize itself against dislodgement, or to stabilize the adjacent vertebrae.

A review of all possibly related prior art will demonstrate the novelty of the present invention.

There have been an extensive number of attempts to develop an acceptable disc prothesis (an artificial disc). Such devices by design would be used to replace a damaged disc and seek to restore the height of the interspace and to restore the normal motion of that spinal joint. No such device has been found that is medically acceptable. This group of prosthetic or artificial disc replacements seeking to preserve spinal motion which are different from the present invention include:

U.S. Pat. No. 3,867,728 STUBSTAD—describing a flexible disc implant.

U.S. Pat. No. 4,349,921 KUNTZ—describing a flexible disc replacement with rope or file like surface projections to discourage device dislocation.

U.S. Pat. No. 4,309,777 PATIL—describing motion preserving implant with spice outer surfaces to resist dislocation and containing a series of springs to urge the vertebrae away from each other.

U.S. Pat. No. 3,875,595 FRONING—describing a motion preserving bladder like disc replacement with two opposed stud like projections to resist dislocation.

U.S. Pat. No. 2,372,622 FASSIO (French)—describing a motion preserving implant comprising complimentary opposed convex and concave surfaces.

In summary then, these and other similar devices resemble the present invention only in that they are placed within the intervertebral space following the removal of a damaged disc. In that they seek to preserve spinal motion, they are diametrically different from the present invention which seeks to permanently eliminate all motion at that spinal segment.

A second related area of prior art includes those devices utilized to replace essentially wholly removed vertebra. Such removal is generally necessitated by extensive vertebral fractures, or tumors, and is not associated with the treatment of disc disease, or therefore related to the present invention. While the present invention is to be placed within the disc space, these prior devices cannot be placed within the disc space as at least one vertebra has already been removed and there no longer remains a "disc space." Furthermore, all of these devices are limited in that they seek to perform as temporary structural members mechanically replacing the removed vertebra (not a removed disc), and do not intrinsically participate in supplying osteogenic material to achieve cross vertebrae bony fusion. Therefore, again unlike the present invention which provides for a source of osteogenesis, use of this group of devices must be accompanied by a further surgery consisting of a bone fusion procedure utilizing conventional technique. This group consisting of vertebral struts rather than disc replacements would include the following:

U.S. Pat. No. 4,553,273 WU—describing a turnbuckle like vertebral strut.

U.S. Pat. No. 4,401,112 REZAIAN—describing a turnbuckle like vertebral strut with the addition of a long stabilizing staple that spans the missing vertebral body.

U.S. Pat. No. 4,554,914 KAPP—describing a large distractible spike that elongates with a screw mechanism to span the gap left by the removal of a entire vertebrae and to serve as an anchor for acrylic cement which is then used to replace the missing bone (vertebrae).

U.S. Pat. No. 4,636,217 OGILVIE—describing a vertebral strut mechanism that can be implanted after at least one vertebra has been removed and which device consists of a mechanism for causing the engagement of screws into the vertebra above the vertebra below the one removed.

In summary then, this group of devices differs from the present invention in that they are vertebral replacement struts, do not intrinsically participate in the bony fusion, can only be inserted in the limited circumstances where an entire vertebra has been removed from the anterior approach, and are not designed for, or intended to be used for the treatment of disc disease.

A third area of prior art related to the present invention includes all devices designed to be applied to one of the surfaces of the spine. Such devices include all types of plates, struts, and rods which are attached by hooks, wires, and screws. These devices differ significantly from the present invention in that they are not inserted within the disc space, and furthermore do not intrinsically participate in supplying osteogenic material for the fusion.

Therefore, with these devices where permanent spinal immobilization is desired an additional surgery consisting of a spinal fusion performed by conventional means or the use of supplemental methylmethacrylate cement is required. Such devices, applied to the spine but not within the disc space, would include the following:

U.S. Pat. No. 4,604,995—STEPHENS—describing a "U" shaped metal rod attached to the posterior elements of the spine with wires to stabilize the spine over a large number of segments.

U.S. Pat. No. 2,677,369—KNOWLES—describing a metal column device to be placed posteriorly along the lumbar spine to be held in position by its shape alone and to block pressure across the posterior portions of the spinal column by locking the spine in full flexion thereby shifting the maximum weight back onto the patient's own disc.

Other devices are simply variations on the use of rods (e.g. Harrington, Luque, Cotrel-Dubosset, Zielke), wires or cables (Dwyer), plates and screws (Steffee), or struts (Dunn, Knowles).

In summary, none of these devices are designed for or can be used within the disc space, do not replace a damaged disc, and do not intrinsically participate in the generation of a bony fusion.

Other prior art possibly related to the present invention and therefore, to be considered related to "Bony Ingrowth". Patents related to this feature describe either methods of producing materials or devices to achieve the same. Such patents would include:

U.S. Pat. No. 4,636,526 (DORMAN), U.S. Pat. No. 4,634,720 (DORMAN), U.S. Pat. No. 4,542,539 (ROWE), U.S. Pat. No. 4,405,319 (COSENTINO), U.S. Pat. No. 4,439,152 (SMALL), U.S. Pat. No. 4,168,326 (BROEMER), U.S. Pat. No. 4,535,485 (ASHMAN), U.S. Pat. No. 3,987,499 (SCHARBACH), U.S. Pat. No. 3,605,123 (HAHN), U.S. Pat. No. 4,655,777 (DUNN), U.S. Pat. No. 4,645,503 (LIN), U.S. Pat. No. 4,547,390 (ASHMAN), U.S. Pat. No. 4,608,052 (VAN KAMPEN), U.S. Pat. No. 4,698,375 (DORMAN), U.S. Pat. No. 4,661,536 (DORMAN), U.S. Pat. No. 3,952,334 (BOKROS), U.S. Pat. No. 3,905,047 (LONG), U.S. Pat. No. 4,693,721 (DUCHEYNE), U.S. Pat. No. 4,070,514 (ENTHERLY).

However, while the present invention would utilize bone ingrowth technology, it would do so with conventional technology.

The final area of related prior art to be considered is that of devices designed to be placed within the vertebral interspace following the removal of a damaged disc, and seeking to eliminate further motion at that location.

Such a device is contained in U.S. Pat. No. 4,501,269—BAGBY describing an implantable device, limited instrumentation, and a method; whereby a hole is bored transversely across the joint and then a hollow metal basket of larger diameter is then pounded into the hole and then filled with the bone debris generated by the drilling. The present invention differs from the prior art devices in the following ways:

1. UNIVERSAL APPLICABILITY WITHOUT CONTOURING OF THE INTERSPACE. The present device will fit any patient, anywhere throughout the spine, in any intervertebral disc space, and without alteration of that interspace regardless of its natural size or shape.

2. RESTORATION AND PRESERVATION OF THE INTERSPACE. The present invention will restore the intervertebral space to its premorbid dimensions, and do so by having the implant fit the space rather than having to modify the interspace, by bone removal from the vertebrae, to accommodate the implant.

3. END PLATE PRESERVATION. Preservation of the highly specialized weight bearing cortical bone is allowed and end plate perforation into the highly vascular cancellous bone marrow with its attendant bleeding is avoided. Such bleeding, when it occurs, bears all the risks of blood loss (e.g. hypovolemic shock, transfusion transmitted diseases such as hepatitis and acquired immune deficiency syndrome, etc.), and all the complications arising from the resultant impaired visualization of the vital structures (e.g. nerves, blood vessels, and organs) due to such bleeding.

4. TECHNIQUE. The technique for insertion of these implants is consistent with the established methods of disc removal, and requires neither specialized instrumentation nor specialized surgical technique.

5. EXTENT OF DISC REMOVAL. The extent of disc removal can be determined by the surgeon at the time surgery and can be individualized for each patient.

6. NO DRILLING. No drilling is involved with the use of the present invention.

7. ELIMINATION OF INCORRECT IMPLANT SIZE SELECTION. In those implant systems where a drill is used and significant bone is removed then an estimate of the implant size must first be made, and then, regardless of the fit, an implant at least as large as the space created by the drilling must be utilized, regardless of the quality of that fit. With the present invention no significant bone is removed, and the correct size implants are fitted directly to the interspace eliminating the need to guess at the correct implant size before the fact.

8. MODULAR DESIGN. The present implants are available in varying lengths to accommodate the changing depths of the interspace from central to lateral. The devices are available in varying heights or are infinitely adjustable as to the height within the physiological range. The widths are standardized, and the various embodiments can be used in any combination (e.g. in the lumbar spine two auto-expanding implants could be used in conjunction with two anchor deploying implants to completely fill the interspace).

9. AVOIDANCE OF SIZE LIMITATIONS. Because in one embodiment the system is modular, component parts can be inserted through a very small opening until a much larger implant is reconstituted completely filling the available interspace; and yet much larger when assembled than the opening through which the component modular sections were introduced. For example, in the lumbar spine four implants introduced one at a time and measuring 8 mm in width, would when reconstituted within the interspace constitute a 32 mm wide implant. Implantation of a single implant of those dimensions from a posterior approach in the lumbar spine would otherwise be impossible because of the presence of the dural sac and spinal nerves.

10. THE AVOIDANCE OF INTERSPACE COLLAPSE. The device is many times stronger than bone and will not collapse. The implantation of the device allows preservation of the very strong vertebral cortex, which is resistant to compression preventing the migration of the implant into the vertebrae. The large surface area of the assembled modular implant, minimizes the load per unit area. For example, a reconstituted lumbar implant of four modular components would have the weight distributed over approximately 8 sq. cm. per vertebral interface.

11. REMOVABILITY. Because the present invention is an interspace implant and not a "through vertebrae" cross interspace implant, removal of the implant, should that become necessary, would not result in iatrogenic destruction of the adjacent vertebrae.

12. SELF-STABILIZING. The implant is self-stabilizing without the use of threads. All of the implants are surface configured to resist dislodgement and the preferred embodiments contain active, mechanical means to assure permanent anchoring. Long term stability begins with the above and is further enhanced by surface treating of the implant for bone ingrowth (by known conventional means) and osteogenically loading the implants.

13. SPINE REDUCING. Various embodiments of the present invention such as the ones with the 180 degree opposed ratcheted surface, and the auto-expanding type, are capable of reducing a vertebral listheses (a forward or backward translation of one vertebrae upon another).

14. SPINAL STABILITY. These implants are capable of stabilizing a spinal segment following disc removal, and do so without the use of threads (threads would by design need to violate the vertebrae themselves extensively).

15. SAFETY. The entire procedure is performed under direct vision and with complete visualization of the adjacent vital structures (e.g. organs, neural structures and blood vessels).

In summary then, the present invention is an interspace implant utilized to replace a damaged disc, which unlike an artificial disc, seeks to permanently eliminate rather than to preserve spinal motion, and to do so by a bony fusion. The present invention is clearly an improvement over the prior art providing an interspace implant intrinsically participating in the fusion process, self-stabilizing, stabilizing to the spinal segment, consistent with conventional methods of discectomy, and uniquely consistent with the preservation of the integrity of the adjacent vertebrae.

BRIEF SUMMARY OF THE PRESENT INVENTION

The present invention comprises an artificial implant, the purpose of which is to participate in, and directly cause bone fusion across an intervertebral space following the excision of a damaged disc. Said implants are structurally load bearing devices, stronger than bone, capable of withstanding the substantial forces generated within the spinal interspace. Such devices have a plurality of macro sized openings of 1–3 mm, which can be loaded with fusion promoting materials, such as autogenous bone, for the purpose of materially influencing the adjacent vertebrae to perform a bony bond to the implants and to each other. The implant casing may be surface textured or otherwise treated by any of a number of known technologies to achieve a "bone ingrowth surface" to further enhance the stability of the implant and to expedite the fusion. Further, said devices are so configured and designed so as to promote their own stability within the vertebral interspace to resist dislodgement, and furthermore, to stabilize the adjacent vertebrae.

To use the implant of the present invention a conventional discectomy is performed and the vertebral endplates scraped, but not perforated. The appropriately sized implants are loaded with autogenous bone and implanted within the interspace.

For example for an anterior cervical device implantation, a short transverse incision is made across the front of the neck and to the right of the midline directly over the diseased disc. The platysma muscle is split, and the sternocleidomastoid muscle with the carotid sheath is protected and retracted laterally. The esophagus, trachea and associated midline structures are protected and retracted medially, thus exposing the anterior aspect of the cervical spine. The diseased disc is identified and removed by conventional surgical methods. The adjacent vertebral endplates are gently scraped free of any remaining cartilage until diffuse fine punctuate decortication is achieved. The dimensions of the interspace are then measured In mold distraction, and the appropriate implant selected. Cancellous bone, obtained from the patient's iliac crest or the equivalent, is loaded into the implant. The safety driver is then utilized to insert the implant behind the anterior lips of the vertebrae. The wound is then closed in the routine manner.

OBJECTS OF THE PRESENT INVENTION

It is an object of the present invention to provide for a means of achieving interspace fusion and stabilization as a single procedure by a means consistent with the conventional method of discectomy.

It is another object of the present invention to provide for a means of achieving an interspace fusion and stabilization that is quicker, safer, and entails less blood loss than by any other known means.

It is another object of the present invention to provide for a means of achieving a one stage interspace fusion and stabilization without significant violation or removal of the adjacent vertebral bone stock.

It is another object of the present invention to provide for a method of intervertebral arthrodesis and stabilization of enhanced safety where the entire procedure is performed under direct vision.

It is another object of the present invention to provide for a method of intervertebral arthrodesis and stabilization of greater simplicity and requiring minimal specialized instrumentation or technique not already possessed by those doing such procedures by conventional means.

It is another object of the present invention to provide for a modular prosthesis, allowing complimentary subunits to be inserted individually through a small opening and to then be reassembled within the interspace, so as to reconstitute an interspace occupying device much larger than would be insertable as a whole.

It is another object of the present invention to provide for a modular implant system such that it is possible to precisely fit the contours of any interspace without the need to sacrifice any vertebral bone to accommodate the prosthesis. These and other objects of the present invention will be apparent from review of the following specifications and the accompanying drawings.

BRIEF DESCRIPTION OF THE DRAWINGS

FIG. 1c is a top view of the implant of FIG. 1.

FIG. 1d is a side view of the implant of FIG. 1.

FIG. 1e is a bottom view of the implant of FIG. 1.

FIG. 2 is a side sectional view of the implant viewed along lines 2—2 of FIG. 1d.

Referring to FIGS. 1 through 5 an implant for use in the disc space and associated apparatus used for inserting the implant 10 is shown. The implant 10 is shown as a substantially rectangular hollow configuration, having a tapered forward portion.

Figure 1:
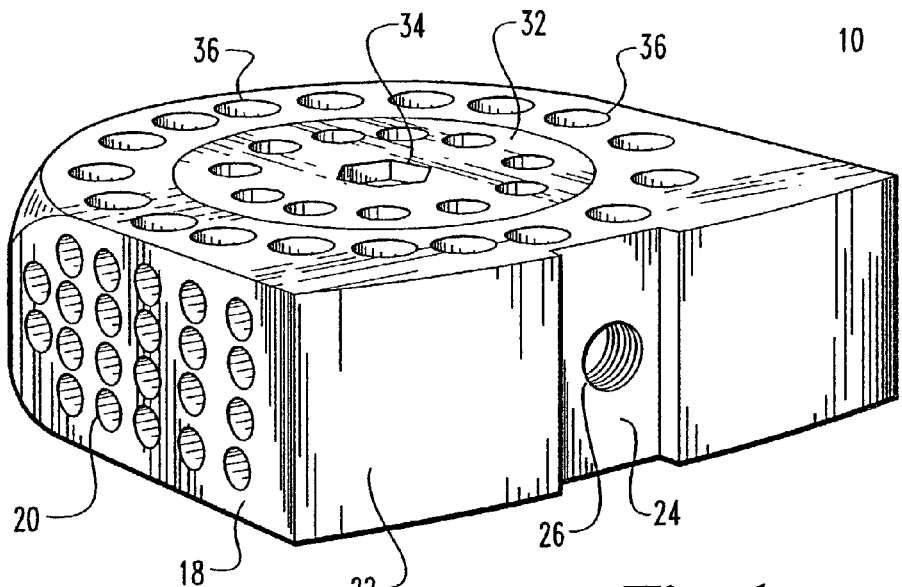
FIG. 1 is a top right perspective view of the implant (cervical type).
Figure 1A:
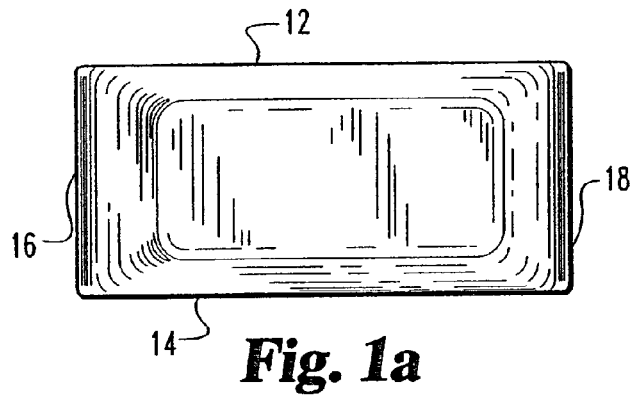
FIG. 1a is a front view of the implant of FIG. 1
Figure 1B:
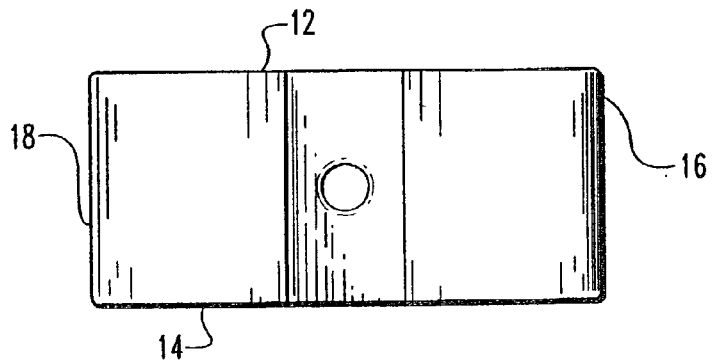
FIG. 1b is a rear view of the implant of FIG. 1.

The implant 10 has an upper surface 12 and a parallel lower surface 14. The two side walls 16 and 18 are parallel to one another and have a series of small sized openings 20 of 1 mm–3 mm through the side walls 16 and 18.

The front wall 22 is slightly convex and has a depressed portion 24 with a central threaded opening 26 for receiving the engaging end 28 of a driving member 30.

Figure 3:
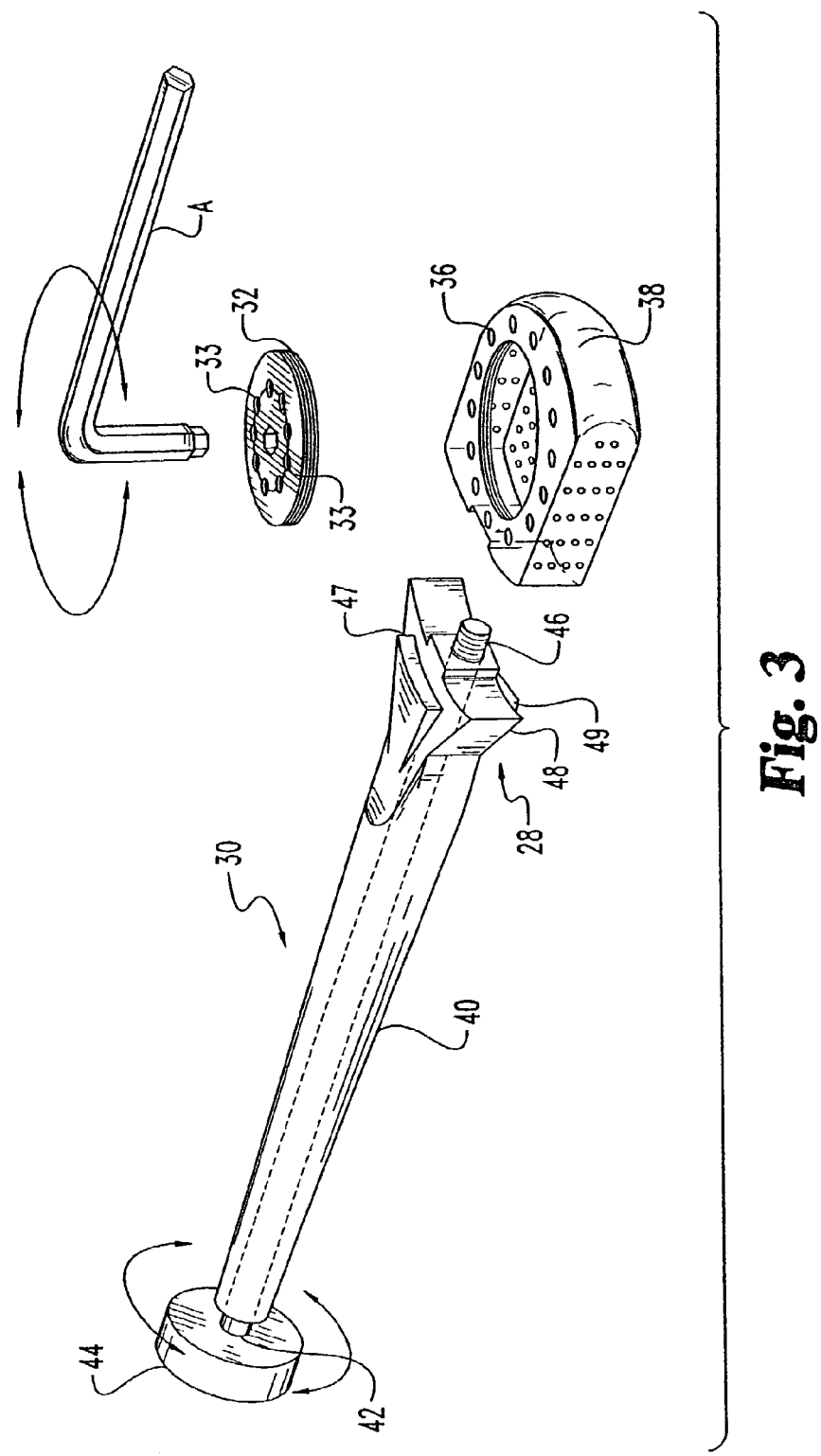
FIG. 3 is the implant FIG. 1 showing the attachment to the driver and driver.

The upper surface 12 has a threaded cap 32, which has opening 33 there through, with a central wrench opening 34 for engagement with an ALLEN hex key wrench A of FIG. 3. The cap 32 covers the opening into the hollow implant 10 and permits the insertion of autogenous bone material into the hollow portion of the implant 10. The cap 32 is surrounded by a series of small sized openings 36 of 1 mm to 3 mm passing through the upper surface and into the central hollow portion of the implant 10.

The rear wall 38 is convex so as to conform to the rear of the disc space.

The driving member 30, shown in FIG. 3, comprises a substantially hollow tubular member 40 having a long internal rod 42 having a turning knob 44 at one end and a threaded portion 46 at the other end for threadably engaging the threaded opening 26 of the implant 10. The engaging end 28 of the driving member 30 has a slightly convex surface to complement the slightly convex surface of the front wall 22. The engaging end 28 has an extension 48 for fitting within the depressed portion 24 on the front wall 22 of the implant 10. The engaging end 28 also has restriction members 47 and 49 to restrict the depth of penetration of the driver 30.

In use, the cap 32 is removed from the implant 10 and autogenous bone material is inserted into the hollow portion of the implant 10. The cap is then replaced. Various methods of packing the implant 10 with the autogenous bone material may be used to obtain a completely packed implant 10.

Referring to FIGS. 4, 4a, 5 and 5a, the method of inserting the implant is shown. The threaded end 46 of the internal rod 42 of the driving member 30 is attached to the threaded opening 26 of the implant 10 by turning of the knob 44. Once the engaging end 28 is in place, the fitting of the extended portion 48 into the depressed portion 24 prevents movement of the implant 10 in relationship to the driving member 30.

The implant is then placed at the entrance to the disc space between the two adjacent vertebrae V. The knob 44 is then tapped with hammer 11 sufficiently hard enough to drive the implant 10 into the disc space. The restriction members 47 and 49 which are wider than the disc space, prevent over penetration of the implant.

The size of the implant 10 is substantially the same size as the disc space that it is replacing and thus will be larger or smaller depending on the disc space in which it is to be used. In the preferred embodiment the implant 10 is approximately 13 mm wide.

Figure 4:
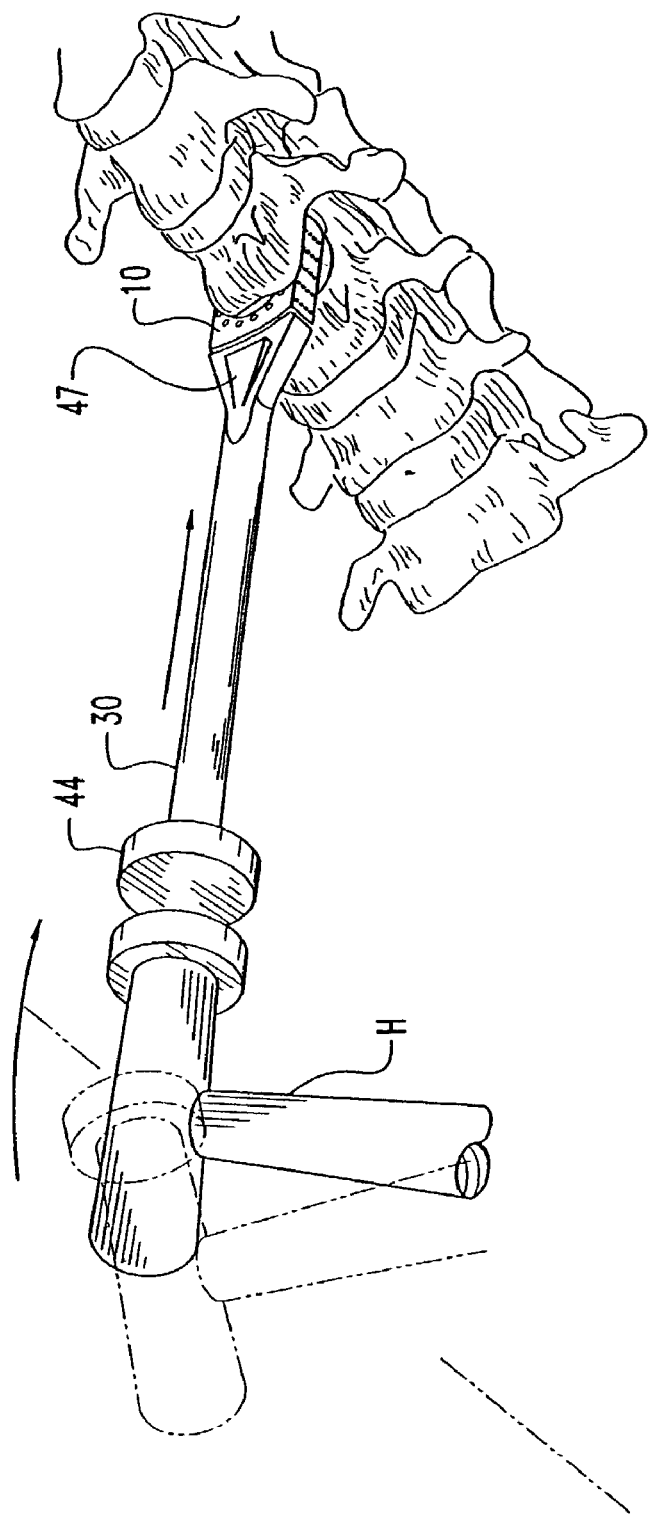
FIG. 4 is a front perspective view showing the implant being driven into the disc space.
Figure 4A:
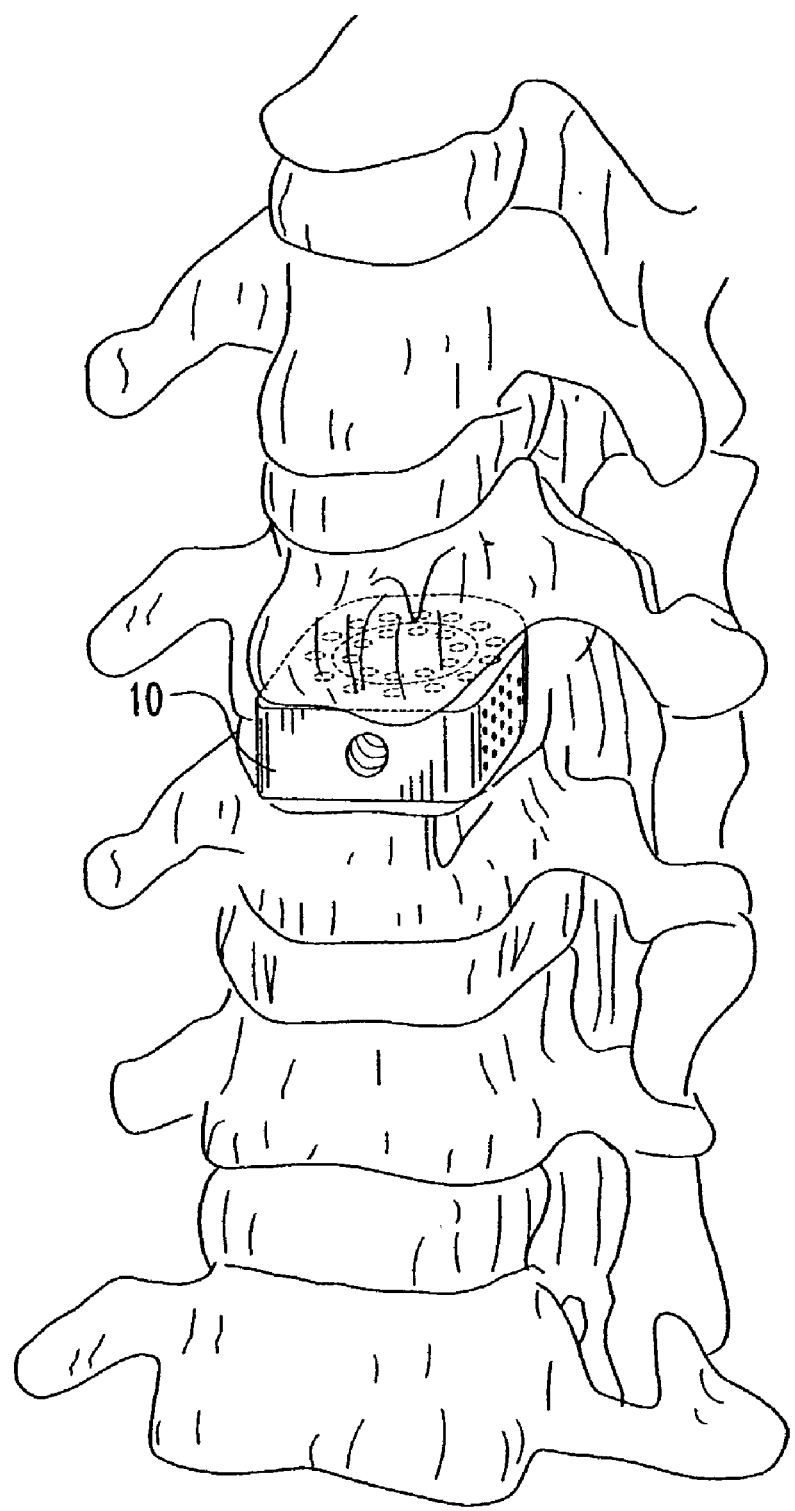
FIG. 4a is a front perspective view of the implant located in the spine.
Figure 5:
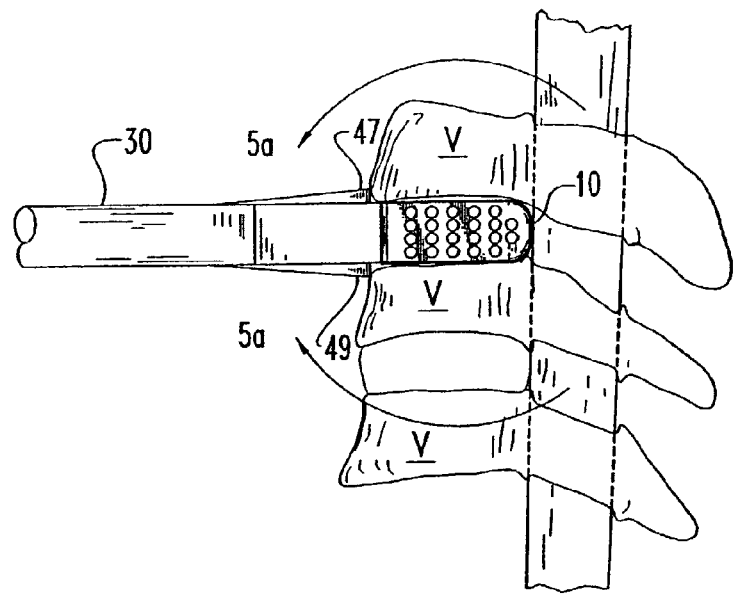
FIG. 5 is a side view of the implant in the spine attached to the driver.
Figure 5A:
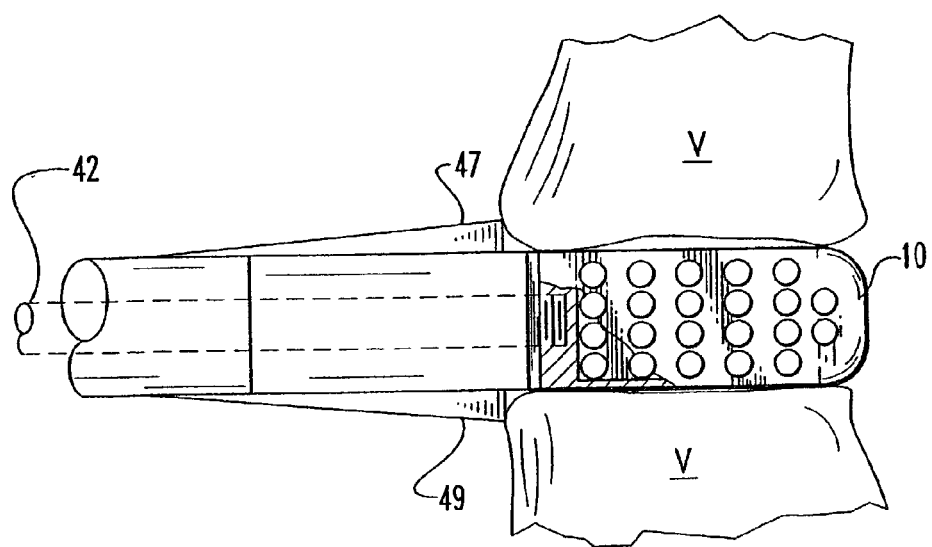
FIG. 5a is a close up partial sectional view of the implant and driver.

Referring to FIGS. 4A and 5 the implant 10 is shown in place in the disc space after removal of the driving member once the implant was inserted in place.

The autogenous bone material that was packed within the hollow portion of the implant 10 serves to promote bone ingrowth between the implant and the adjacent vertebrae. Once the bone ingrowth occurs, the implant 10 will be a permanent fixture preventing dislodgement of the implant as well as preventing any movement between the adjacent vertebrae.

Figure 6:
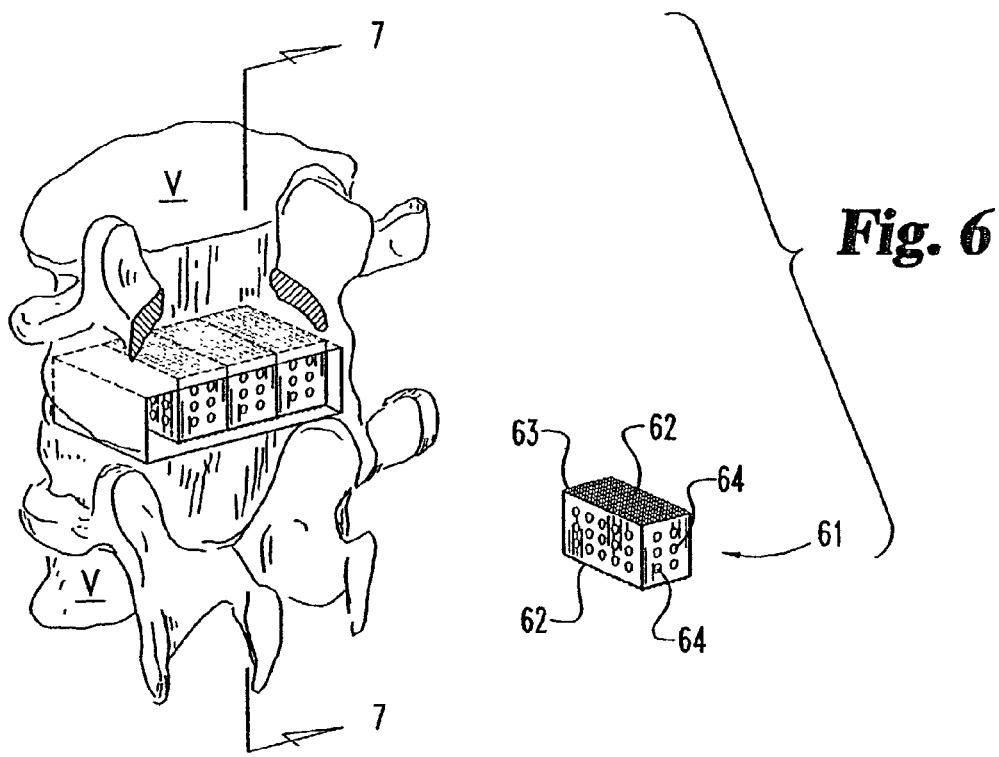
FIG. 6 is a perspective view of a series of implants placed in a lumber intervertebral space.

Referring to FIG. 6 an alternative embodiment of the implant is disclosed. The implant 61 comprises a substantially rectangular member having a series of ridges 62 on the upper and lower surfaces of the implant 60. One or more grooves 64 are placed on the upper and lower surfaces as well. As indicated in FIG. 6, a series of such implants 61 are used as the interbody spinal implant, each placed closely adjacent one another to approximate the size of the removed disc. A series of micro sized openings 63 perforate the implant 61, to promote bone ingrowth.

The implant of FIG. 6 is inserted as follows: the disc is substantially removed by conventional means. The implants 61 are then inserted in the intervertebral space between the two vertebrae.

The size of the implant 61 of FIG. 6 is approximately 26 millimeters in length and is wide enough so that four of them will substantially fill the intervertebral space, depending on which vertebras are fused.

Figure 6A:
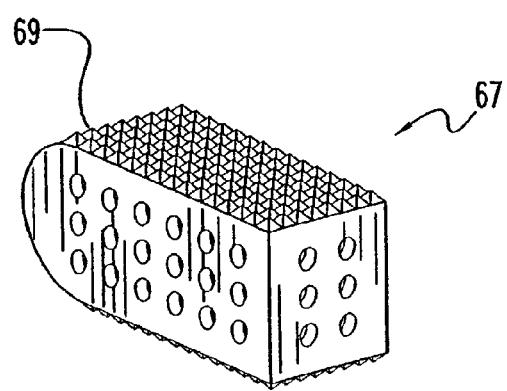
FIG. 6A is an alternative embodiment of a rectangular solid implant.

In FIG. 6a a "bullet nosed" implant 67 having a open front portion 69 to facilitate insertion of implant 67 is shown.

Figure 7:
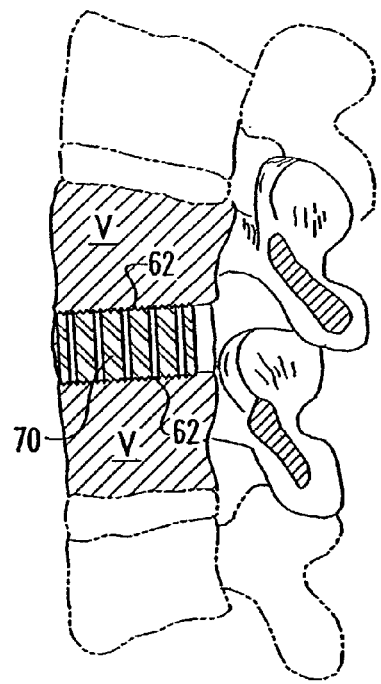
FIG. 7 is a side sectional view of the vertebrae and implant viewed along lines 7—7 of FIG. 6.
Figure 7A:
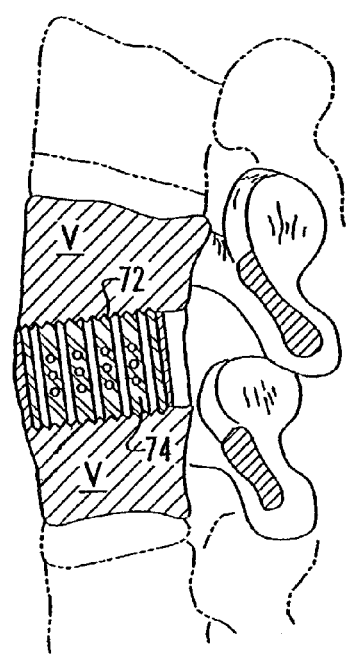
FIG. 7A is a side sectional view of the vertebrae structure showing a third embodiment of the rectangular solid implant in place.

Referring to FIGS. 7 and 7a alternative embodiments of the implant 61 of FIG. 6 is shown in place between two vertebrae V.

In FIG. 7 the implant 70 is shown with the ridges 62 shown in the form of teeth facing the anterior. These ridges serve to prevent the implant 60 from 'walking' out of the space between the vertebrae.

In FIG. 7a an embodiment of the implant 70 of FIG. 6 is shown having opposed ridges 72 and 74. This serves to maintain the alignment of the vertebrae when the two vertebrae V are improperly aligned with respect to one another.

Figure 8:
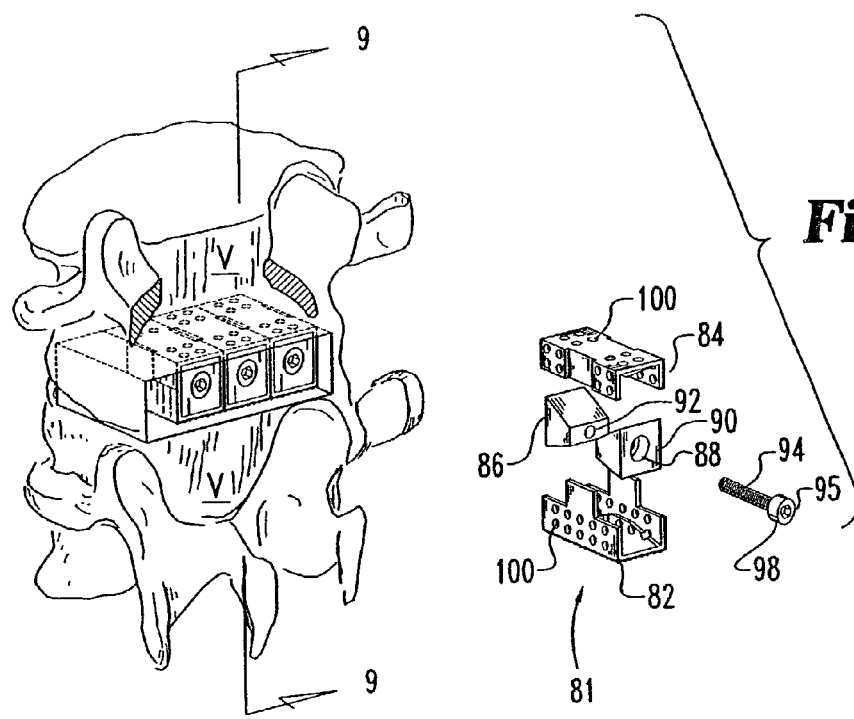
FIG. 8 is an exploded perspective view of another embodiment of the present invention.

Referring to FIG. 8 an adjustable implant 81 having means for adjusting the width of the implant 81 is shown. The implant 81 comprises a lower member 82 and an upper member 84 which when fitted together form an essentially rectangular implant. The upper member 84 and the lower member 82 have hollow portions that face one another and receive tapered wedges 86 and 88 that fit within the hollow portion of the upper and lower members 82 and 84. The wedges 82 and 84 are such that at their large and they are higher than the combined hollow space between the upper and lower members 84 and 82, and shallower at the other end than the hollow space between the upper and lower members.

The wedges 86 and 88 have a central threaded opening 90 and 92 in alignment with each other for receiving threaded screw 94. Deformable burrs 95 on the head 98 of the screw 94 are used for locking the screw in place. The implant has a series of holes 100 throughout the body of the implant to assist in the ingrowth process.

Figure 9:
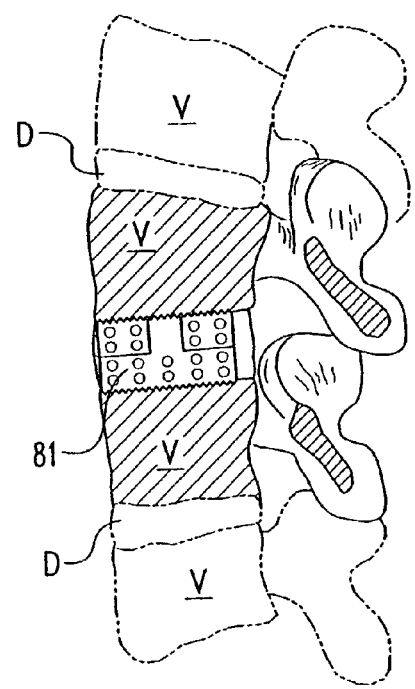
FIG. 9 is a side sectional view of the vertebrae structure and implant viewed along lines 9—9 of FIG. 8.
Figure 10:
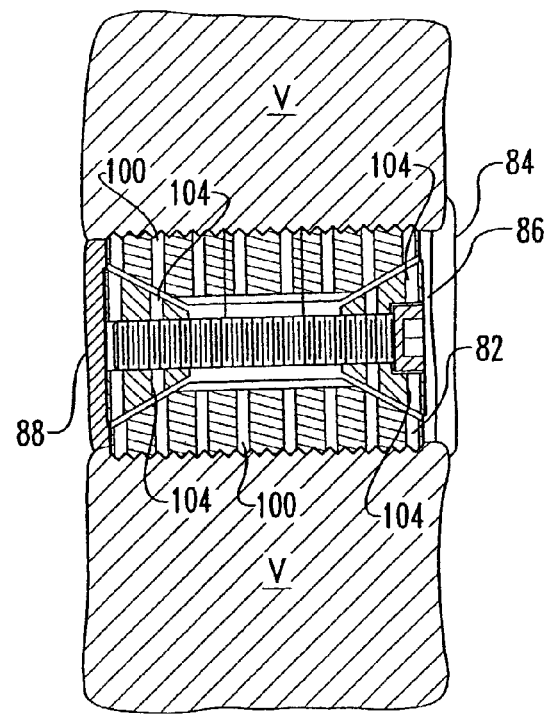
FIG. 10 is a side sectional view of the implant of FIG. 8, in a contracted position.
Figure 11:
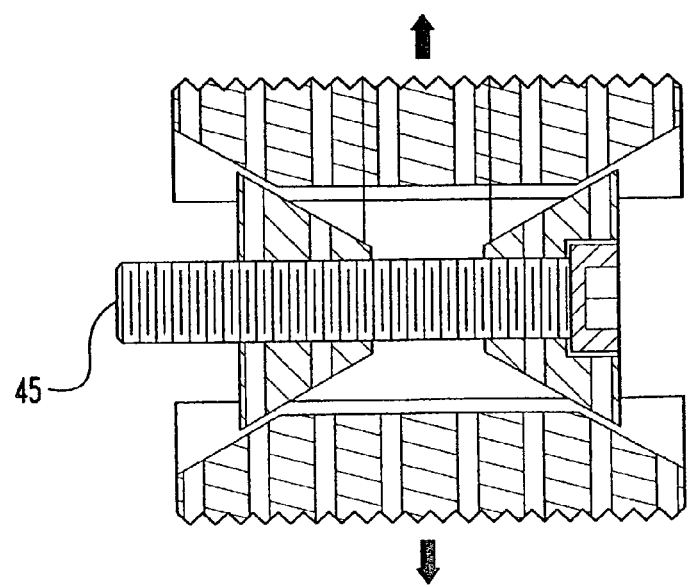
FIG. 11 is a side sectional view of the implant of FIG. 10, in an expanded position.

Referring to FIGS. 9 through 11 the expandable implant 81 is shown positioned between the two vertebrae V. In FIG. 10 the expandable implant 81 is illustrated in its contracted position. The wedges 86 and 88 abutt the interior sloped surfaces 104 of the upper and lower members 82 and 84.

As the screw 94 is turned, as shown in FIG. 11, the wedges 86 and 88 are drawn together, and the sloped portions of the wedges force the upper member 82 away from the lower member 84. Once the screw 94 has been turned sufficiently, the screw head 98 is hit, causing the deformable burrs to be crimped so as to prevent the reverse rotation of the screw 94.

Figure 12:
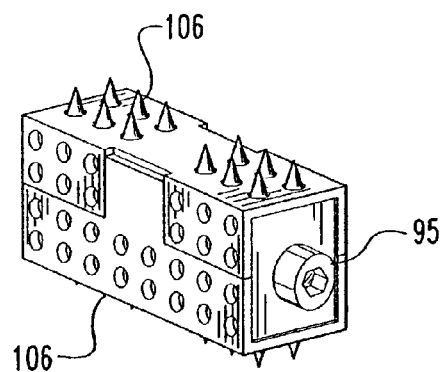
FIG. 12 is a perspective view of an alternative embodiment of the implant of FIG. 9.

In FIG. 12, another alternative embodiment of the expandable implant 81 is illustrated with spike projections 106 extending from the top and bottom members to dig into the vertebrae and assist in maintaining it in place.

In use, the disc is removed, and the implant 81 is placed between the vertebrae. The screw 94 is then turned expanding the implant. In the preferred embodiment, the width is from 8 millimeters to 18 millimeters.

Figure 13:
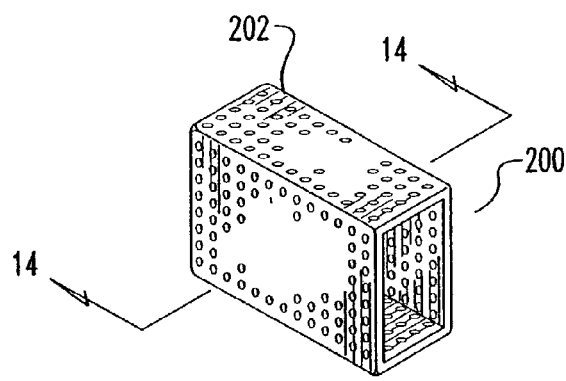
FIG. 13 is an alternative embodiment of a hollow rectangular solid implant.
Figure 14:
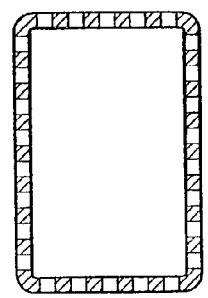
FIG. 14 is a cross sectional view of the hollow rectangular solid implant of FIG. 13 viewed along lines 14—14 of FIG. 13.

Referring to FIGS. 13 and 14, another alternative embodiment of the invention is shown in which the implant 200 comprises a rectangular hollow member having a slightly tapered forward section 202. The cross section, shown in FIG. 14, shows the rectangular configuration of the implant.

In use of the implant the interior of the implant is filled with a paste made of autogenous bone, and inserted in the place of the former disc. The strength of the material used to make the implant is such that, even though it is substantially hollow, it does have sufficient strength to withstand the forces of the vertebrae compressing the implant.

Figure 15:
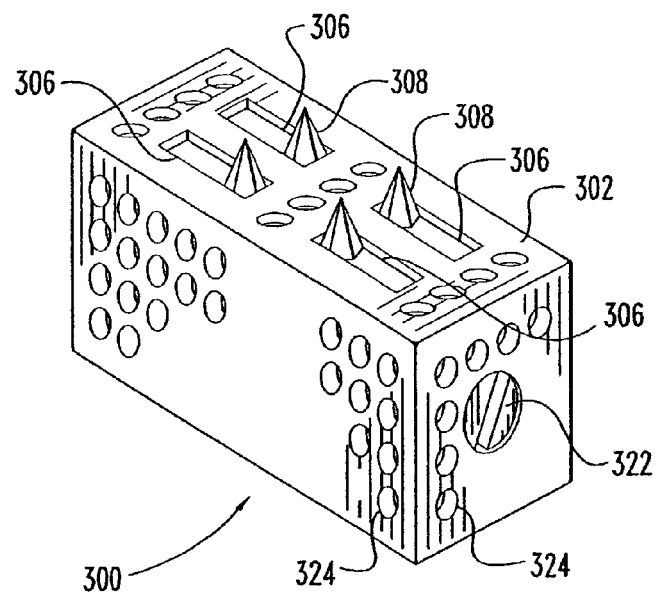
FIG. 15 is an alternative embodiment of an expandable implant in its extended position.
Figure 16:
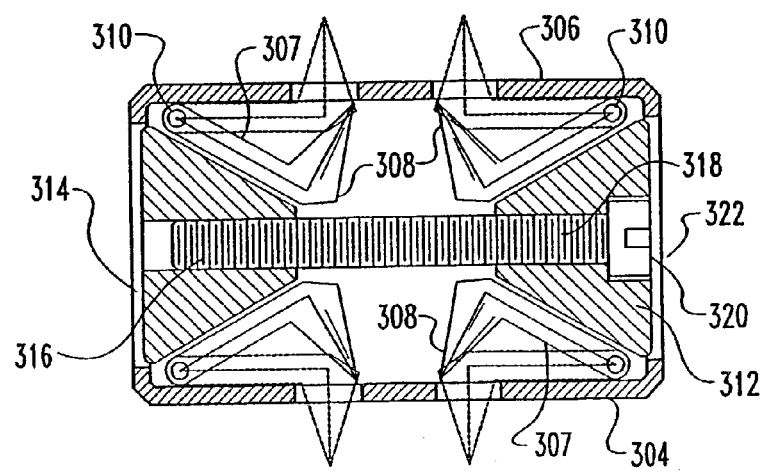
FIG. 16 is an expandable implant of FIG. 15 in its retracted position.
Figure 17:
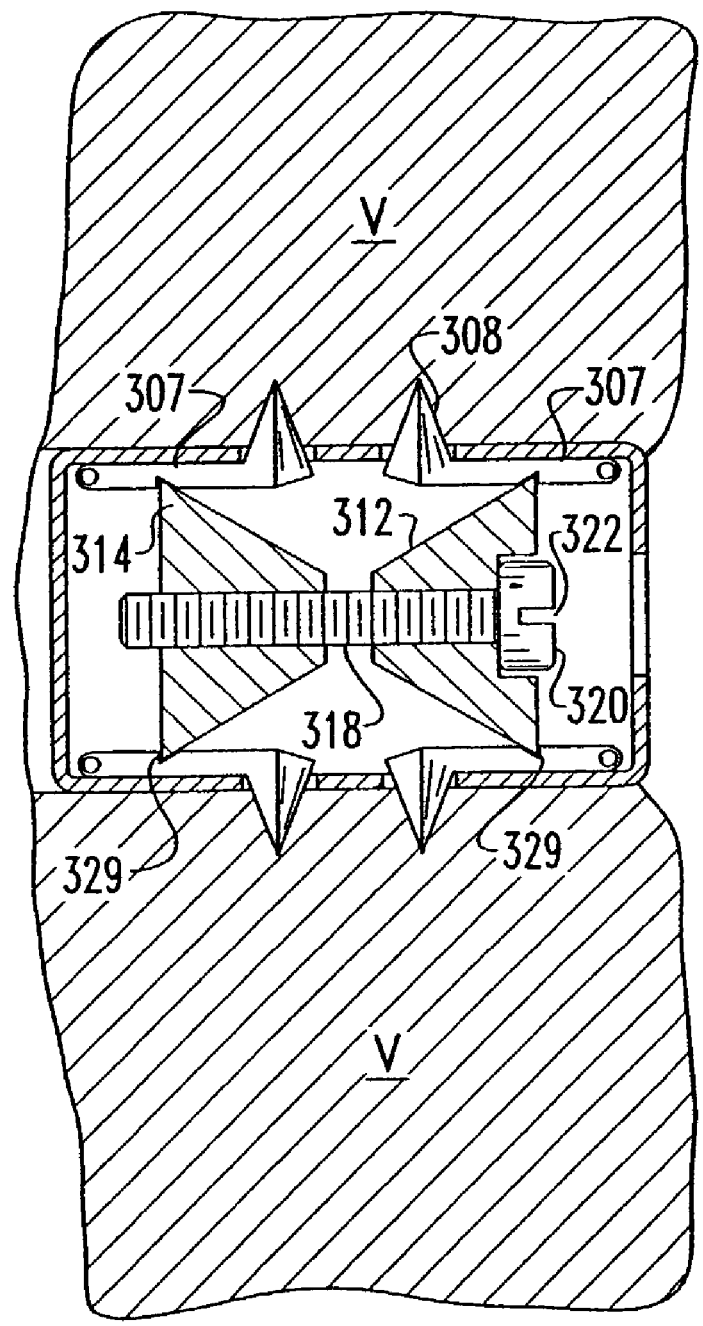
FIG. 17 is an expandable implant of FIG. 16 located in the disc space.

Referring to FIGS. 15–17, another alternative embodiment is shown in which the implant has movable projections which are movable from a first position within the implant to a second position extending outside of the implant.

The implant 300 is of a generally rectangular configuration. The top surface 302 and the bottom surface 304 of the implant have slots 306 for permitting pivotal member 307 having spikes 308 at their ends to project through said slots 306. The spikes 308 are pinned at one end 310 within the implant 300.

Opposing wedge shaped members 312 and 314 having a central threaded opening 316 for receiving a threaded screw 318 having a head 320 and a slot 322. The wedges are facing each other so that upon turning of the screw will draw the two wedges together, causing the wedges to cause the spikes 308 to pivot about their end 310 and cause the spikes to project out of the implant through the aligned slots 306. The depressions 329 in the pivotal member 307 engage the wedges 314 and 312 to lock the pivotal members 307 in place. A series of holes 324 for promoting bone ingrowth and fusion are provided in the implant 300.

In use, after the removal of the disc material, the implants with the spikes 308 in their withdrawn position, are inserted into the disc space. Then the screw 318 is turned until the spikes 308 are forced to enter the vertebrae material, as shown in FIG. 17. The implant 300 is thus held firmly in place.

These implants have a surface configuration so as to induce bone ingrowth through the implant, and into the wall of the vertebrae in effect inducing fusion from one vertebrae V to the other, thereby eventually making the implant itself superfluous as the bone would do the work.

The implant itself, because of its being made of stronger material than bone, would provide structural support to the two vertebrae while awaiting bone ingrowth. Once the bone ingrowth occurred, however, the implant would be firmly and permanently fixed in place.

While the invention has been described with regards to the preferred embodiment and a number of alternative embodiments, it is recognized that other embodiments of the present invention may be devised which would not depart from the scope of the present invention.

What is claimed is:

1. A spinal fusion implant comprising:
   a leading end and a trailing end opposite said leading end, said implant having a length from said leading end to said trailing end, said trailing end having a perimeter, said trailing end having a hole therein, said trailing end having a slot portion intersecting one portion of the perimeter of said trailing end, said trailing end having another slot portion intersecting another portion of the perimeter of said trailing end opposite said one portion of the perimeter of said trailing end;
   opposite sides between said leading and trailing ends, said implant having a width from one of said sides to the other of said sides, said implant having a height; and
   an opening through said implant and oriented along the height, said opening being between said opposite sides and between said leading and trailing ends.

2. The implant of claim 1, wherein said slot portion and said another slot portion are opposite ends of a slot having a length and a width transverse to the length of said slot.

3. The implant of claim 2, wherein said hole has a diameter, the width of said slot being greater than the diameter of said hole.

4. The implant of claim 2, wherein said slot of said trailing end is rectangular.

5. The implant of claim 2, wherein the length of said slot is greater than the width of said slot.

6. The implant of claim 2, wherein said slot has a depth perpendicular to the length and the width of said slot, the width of said slot being greater than the depth of said slot.

7. The implant of claim 1, wherein said hole is threaded.

8. The implant of claim 2, wherein said hole has a diameter, the diameter of said hole being less than one half the length of said slot.

9. The implant of claim 1, wherein said sides have at least one opening in communication with said opening through the height of said implant.

10. The implant of claim 1, wherein said implant comprises a second opening through said implant and oriented along the height, said second opening being between said opposite sides and between said leading and trailing ends.

11. The implant of claim 1, wherein the height of said implant is less than the width of said implant.

12. A spinal implant comprising:
   a leading end and a trailing end opposite said leading end, said implant having a length from said leading end to said trailing end, said trailing end having a perimeter, said trailing end having a hole therein, said trailing end having a slot portion intersecting one portion of the perimeter of said trailing end, said trailing end having another slot portion intersecting another portion of the perimeter of said trailing end opposite said one portion of the perimeter of said trailing end;
opposite sides between said leading and trailing ends, said implant having a height perpendicular to the length of said implant; and
said implant having a generally rectangular cross section along at least a portion of the length of said implant.

13. The implant of claim 12, wherein said slot portion and said another slot portion are opposite ends of a slot having a length and a width transverse to the length of said slot.

14. The implant of claim 13, wherein said hole has a diameter, the width of said slot being greater than the diameter of said hole.

15. The implant of claim 13, wherein said slot of said trailing end is rectangular.

16. The implant of claim 13, wherein the length of said slot is greater than the width of said slot.

17. The implant of claim 13, wherein said slot has a depth perpendicular to the length and the width of said slot, the width of said slot being greater than the depth of said slot.

18. The implant of claim 12, wherein said hole is threaded.

19. The implant of claim 13, wherein said hole has a diameter, the diameter of said hole being less than one half the length of said slot.

20. The implant of claim 12, further comprising an opening through said implant and oriented along the height, said opening being between said opposite sides and between said leading and trailing ends.

21. The implant of claim 20, wherein said sides have at least one opening in communication with said opening oriented along the height of said implant.

22. The implant of claim 20, wherein said implant comprises a second opening through said implant and oriented along the height, said second opening being between said opposite sides and between said leading and trailing ends.

23. The implant of claim 12, wherein said implant has a width from one of said sides to the other of said sides, the height of said implant being less than the width of said implant.

24. A spinal implant comprising:
a leading end and a trailing end opposite said leading end, said implant having a length from said leading end to said trailing end, said trailing end having a perimeter, said trailing end having a hole therein, said trailing end having a slot portion intersecting one portion of the perimeter of said trailing end, said trailing end having another slot portion intersecting another portion of the perimeter of said trailing end opposite said one portion of the perimeter of said trailing end, said trailing end being convex; and
opposite sides between said leading and trailing ends, said implant having a height perpendicular to the length of said implant.

25. The implant of claim 24, wherein said slot portion and said another slot portion are opposite ends of a slot having a length and a width transverse to the length of said slot.

26. The implant of claim 25, wherein said hole has a diameter, the width of said slot being greater than the diameter of said hole.

27. The implant of claim 25, wherein said slot of said trailing end is rectangular.

28. The implant of claim 25, wherein the length of said slot is greater than the width of said slot.

29. The implant of claim 25, wherein said slot has a depth perpendicular to the length and the width of said slot, the width of said slot being greater than the depth of said slot.

30. The implant of claim 24, wherein said hole is threaded.

31. The implant of claim 25, wherein said hole has a diameter, the diameter of said hole being less than one half the length of said slot.

32. The implant of claim 24, further comprising an opening through said implant and oriented along the height, said opening being between said opposite sides and between said leading and trailing ends.

33. The implant of claim 32, wherein said sides have at least one opening in communication with said opening oriented along the height of said implant.

34. The implant of claim 32, wherein said implant comprises a second opening through said implant and oriented along the height, said second opening being between said opposite sides and between said leading and trailing ends.

35. The implant of claim 24, wherein said implant has a width from one of said sides to the other of said sides, the height of said implant being less than the width of said implant.

36. A spinal implant comprising:
a leading end and a trailing end opposite said leading end, said implant having a length from said leading end to said trailing end, said trailing end having a perimeter, said trailing end having a hole therein, said hole having a diameter, said trailing end having a slot portion intersecting one portion of the perimeter of said trailing end, said trailing end having another slot portion intersecting another portion of the perimeter of said trailing end opposite said one portion of the perimeter of said trailing end, said slot portion and said another slot portion being opposite ends of a slot having a length, said slot having a width transverse to the length of said slot, the width of said slot being greater than the diameter of said hole; and
opposite sides between said leading and trailing ends, said implant having a height perpendicular to the length of said implant.

37. The implant of claim 36, wherein said slot of said trailing end is rectangular.

38. The implant of claim 36, wherein the length of said slot is greater than the width of said slot.

39. The implant of claim 36, wherein said slot has a depth perpendicular to the length and the width of said slot, the width of said slot being greater than the depth of said slot.

40. The implant of claim 36, wherein said hole is threaded.

41. The implant of claim 36, wherein the diameter of said hole is less than one half the length of said slot.

42. The implant of claim 36, further comprising an opening through said implant and oriented along the height, said opening being between said opposite sides and between said leading and trailing ends.

43. The implant of claim 42, wherein said sides have at least one opening in communication with said opening oriented along the height of said implant.

44. The implant of claim 42, wherein said implant comprises a second opening through said implant and oriented along the height, said second opening being between said opposite sides and between said leading and trailing ends.

45. The implant of claim 36, wherein said implant has a width from one of said sides to the other of said sides, the height of said implant being less than the width of said implant.

46. The implant of claim 36, wherein said implant includes a top and a bottom between said leading and trailing ends, and between said opposite sides, said top and said bottom being generally parallel relative to one another.

47. A spinal implant comprising:
  a leading end and a trailing end opposite said leading end, said implant having a length from said leading end to said trailing end, said trailing end having a perimeter, said trailing end having a hole therein, said trailing end having a slot portion intersecting one portion of the perimeter of said trailing end, said trailing end having another slot portion intersecting another portion of the perimeter of said trailing end opposite said one portion of the perimeter of said trailing end, said slot portion and said another slot portion being opposite ends of a slot having a length, said slot having a width transverse to the length of said slot, said slot having a depth perpendicular to the length and the width of said slot, the width of said slot being greater than the depth of said slot; and
  opposite sides between said leading and trailing ends, said implant having a height perpendicular to the length of said implant.

48. The implant of claim 47, wherein said slot of said trailing end is rectangular.

49. The implant of claim 47, wherein the length of said slot is greater than the width of said slot.

50. The implant of claim 47, wherein said hole is threaded.

51. The implant of claim 47, wherein said hole has a diameter, the diameter of said hole being less than one half the length of said slot.

52. The implant of claim 47, further comprising an opening through said implant and oriented along the height, said opening being between said opposite sides and between said leading and trailing ends.

53. The implant of claim 52, wherein said sides have at least one opening in communication with said opening oriented along the height of said implant.

54. The implant of claim 52, wherein said implant comprises a second opening through said implant and oriented along the height, said second opening being between said opposite sides and between said leading and trailing ends.

55. The implant of claim 47, wherein said implant has a width from one of said sides to the other of said sides, the height of said implant being less than the width of said implant.

56. An artificial spinal fusion implant comprising:
  a leading end and a trailing end opposite said leading end, said implant having a length from said leading end to said trailing end, said implant having a height;
  opposite sides between said leading and trailing ends, said implant having a maximum width from one of said sides to the other of said sides, said implant having a maximum height less than the maximum width of said implant; and
  a plurality of openings through said implant and oriented along the height, said openings being between said opposite sides and between said leading and trailing ends.

57. The implant of claim 56, wherein at least a portion of said leading end is tapered.

58. The implant of claim 56, wherein said leading end is convex.

59. The implant of claim 56, wherein said trailing end is convex.

60. The implant of claim 56, wherein said trailing end includes an opening.

61. The implant of claim 60, wherein said opening of said trailing end is threaded.

62. The implant of claim 56, wherein said trailing end has a flat middle portion.

63. The implant of claim 62, wherein said trailing end includes a rounded portion on both sides of said flat portion.

64. The implant of claim 62, wherein said flat portion includes an opening.

65. The implant of claim 64, wherein said opening of said flat portion is threaded.

66. The implant of claim 56, wherein said trailing end includes a threaded opening having a central longitudinal axis, said implant further including a second threaded opening having a central longitudinal axis perpendicular to the central longitudinal axis of said threaded opening of said trailing end.

67. The implant of claim 56, wherein said trailing end includes a trough.

68. The implant of claim 67, wherein said trough is at a middle portion of said trailing end.

69. The implant of claim 67, wherein said trough includes a hole.

70. The implant of claim 56, wherein said sides are generally flat.

71. The implant of claim 56, wherein one of said sides has at least one opening in communication with at least one of said openings oriented along the height of said implant.

72. The implant of claim 71, wherein said one of said sides includes a plurality of openings.

73. The implant of claim 56, wherein one of said sides has at least one opening in communication with at least one of said openings oriented along the height of said implant, said at least one side opening having a central longitudinal axis and a cross-sectional size transverse to the central longitudinal axis of said at least one side opening, the transverse cross-sectional size of said at least one side opening being different from the transverse cross-sectional size of at least one of said openings oriented along the height of said implant.

74. The implant of claim 56, wherein said implant has a cross section along at least a portion of the length of said implant that forms a quadrilateral.

75. The implant of claim 56, wherein a portion of said leading end forms an arc of a first circle from side to side and a portion said trailing end forms an arc of a second circle from side to side, the first and second circles each having a radius that is different from one another.

76. The implant of claim 75, wherein the radius of the first circle is less than the radius of the second circle.

77. The implant of claim 56, wherein said implant includes a top and a bottom, each of said top and said bottom having an interior surface, the interior surfaces of said top and said bottom being spaced apart from one another to define a hollow interior in communication with at least one of said openings.

78. The implant of claim 56, further comprising a material adapted to fill at least a portion of at least one of said openings.

79. The implant of claim 78, wherein said material is adapted to be retained within said at least one of said openings.

80. The implant of claim 56, wherein said trailing end has a middle portion, each of said sides and said middle portion of said trailing end having an upper edge, a portion of said upper edges of said sides and a portion of said upper edge of said middle portion of said trailing end lying generally in a plane.

81. The implant of claim 56, wherein said implant includes a central vertical axis and each of said sides and said trailing end have an upper portion, said openings having an upper portion between said upper portions of said opposite sides, said upper portion of at least one of said openings having a minimum dimension transverse to the central vertical axis of said implant that is greater than the maximum height of said implant.

82. The implant of claim 56, wherein said openings have a central longitudinal axis and a perimeter surrounding the central longitudinal axis, the perimeter of at least one of said openings being arcuate.

83. The implant of claim 56, wherein said implant includes a central vertical axis and each of said sides and said trailing end have an upper portion, said openings having an upper portion between said upper portions of said opposite sides, said upper portion of at least one of said openings having a minimum dimension transverse to the central vertical axis of said implant that is greater than a majority of the maximum width of said implant.

84. The implant of claim 56, wherein said implant includes a central vertical axis and each of said sides and said trailing end have an upper portion, said openings having an upper portion between said upper portions of said opposite sides, said upper portion of at least one of said openings having a minimum dimension transverse to the central vertical axis of said implant that is greater than a majority of the length of said implant.

85. The implant of claim 56, wherein at least a portior of at least one of said openings extends along a vertical line along the entire height of said implant.

86. An artificial spinal fusion implant comprising:
a leading end and a trailing end opposite said leading end, said implant having a length from said leading end to said trailing end;
opposite sides between said leading and trailing ends, each of said sides and said trailing end having an upper portion, said implant having a maximum width from one of said sides to the other of said sides, said implant having a central vertical axis perpendicular to the length and width of said implant, said implant having a height, said implant having a maximum height less than the maximum width of said implant; and
an opening through said implant and oriented along the height, said opening being between said opposite sides and between said leading and trailing ends, said opening having an upper portion between said upper portions of said opposite sides, said upper portion of said opening having a minimum dimension transverse to the central vertical axis of said implant that is greater than the maximum height of said implant.

87. The implant of claim 86, wherein said opening has a central longitudinal axis that is generally coaxial with the central vertical axis of said implant.

88. The implant of claim 86, wherein at least a portion of said leading end is tapered.

89. The implant of claim 86, wherein said leading end is convex.

90. The implant of claim 86, wherein said trailing end is convex.

91. The implant of claim 86, wherein said trailing end includes an opening.

92. The implant of claim 91, wherein said opening of said trailing end is threaded.

93. The implant of claim 86, wherein said trailing end includes a middle portion that is flat.

94. The implant of claim 93, wherein said trailing end includes a rounded portion on both sides of said flat portion.

95. The implant of claim 93, wherein said flat portion includes an opening.

96. The implant of claim 95, wherein said opening of said flat portion is threaded.

97. The implant of claim 86, wherein said trailing end includes a trough.

98. The implant of claim 97, wherein said trough includes a hole.

99. The implant of claim 86, wherein said sides are generally flat.

100. The implant of claim 86, wherein one of said sides has at least one opening in communication with said opening oriented along the height of said implant.

101. The implant of claim 100, wherein said one of said sides includes a plurality of openings.

102. The implant of claim 86, wherein one of said sides has at least one opening in communication with said opening oriented along the height of said implant, said at least one side opening having a central longitudinal axis and a cross-sectional size transverse to the central longitudinal axis of said at least one side opening, the transverse cross-sectional size of said at least one side opening being different from the transverse cross-sectional size of said opening oriented along the height of said implant.

103. The implant of claim 86, wherein said implant has a cross section along at least a portion of the length of said implant that forms a quadrilateral.

104. The implant of claim 86, wherein a portion of said leading end forms an arc of a first circle from side to side and a portion said trailing end forms an arc of a second circle from side to side, the first and second circles each having a radius that is different from one another.

105. The implant of claim 104, wherein the radius of the first circle is less than the radius of the second circle.

106. The implant of claim 86, wherein said implant includes a top and a bottom, each of said top and said bottom having an interior surface, the interior surfaces of said top and said bottom being spaced apart from one another to define a hollow interior in communication with said opening.

107. The implant of claim 86, further comprising a matorial adapted to fill at least a portion of said opening.

108. The implant of claim 107, wherein said material is adapted to be retained within said opening.

109. The implant of claim 86, further comprising a second opening oriented along the height of said implant and between said opposite sides and between said leading and trailing ends.

110. The implant of claim 86, wherein said opening has a central longitudinal axis and a perimeter surrounding the central longitudinal axis, the perimeter of said opening being arcuate.

111. The implant of claim 86, wherein said minimum transverse dimension of said upper portion of said opening is greater than a majority of the maximum width of said implant.

112. The implant of claim 86, wherein said minimum transverse dimension of said upper portion of said opening is greater than a majority of the length of said implant.

113. The implant of claim 86, wherein said upper portion of said opening has a maximum dimension transverse to the central vertical axis of said implant that is less than the maximum width of said implant.

114. The implant of claim 86, wherein at least a portion of said opening extends along a vertical line along the entire height of said implant.

115. An artificial spinal fusion implant comprising:
a leading end and a trailing end opposite said leading end, said implant having a length from said leading end to said trailing end and a maximum width perpendicular to the length;
a top and a bottom between said leading and trailing ends, said implant having a maximum height from said top to said bottom, said implant having a central vertical axis through said top and said bottom;
a plurality of openings in each of said top and said bottom;
said top and said bottom being spaced apart from one another to form an open area therebetween, said openings in said top and bottom being in communication with said open area;
the maximum width of said implant being greater than the maximum height of said implant.

116. The implant of claim 115, wherein at least a portion of said leading end is tapered.

117. The implant of claim 115, wherein said trailing end is convex.

118. The implant of claim 115, wherein said implant has a cross section along at least a portion of the length of said implant that forms a quadrilateral.

119. The implant of claim 115, wherein a portion of said leading end forms an arc of a first circle from side to side and a portion said trailing end forms an arc of a second circle from side to side, the first and second circles each having a radius that is different from one another.

120. The implant of claim 119, wherein the radius of the first circle is less than the radius of the second circle.

121. The implant of claim 115, further comprising a material adapted to fill at least a portion of one of said openings in said top.

122. The implant of claim 121, wherein said material is adapted to be retained within said one of said openings in said top.

123. The implant of claim 115, wherein one of said openings in said top has a minimum dimension transverse to the central vertical axis of said implant that is greater than the maximum height of said implant.

124. The implant of claim 115, wherein at least one of said openings has a central longitudinal axis and a perimeter surrounding the central longitudinal axis, the perimeter of said opening being arcuate.

125. The implant of claim 115, wherein one of said openings in said top has a minimum dimension transverse to the central vertical axis of said implant that is greater than a majority of the length of said implant.

126. The implant of claim 115, wherein at least one of said openings in said top and at least one of said openings in said bottom overlap each other along a vertical line.

127. The implant of claim 115, wherein said trailing end has a middle portion, said top having an outer perimeter at said middle portion of said trailing end and at opposed side portions, the outer perimeter of said top at said opposed side portions and at said middle portion of said trailing end lying generally in a plane.

128. The implant of claim 115, wherein said top and said bottom are generally parallel to one another.

129. The implant of claim 115, wherein at least one of said top and said bottom is generally planar.

130. The implant of claim 115, wherein at least one of said top and said bottom is non-arcuate from side to side.

131. The implant of claim 115, wherein at least one of said top and said bottom includes a portion extending across the entire length of said implant generally halfway along the maximum width of said implant.

132. The implant of claim 115, wherein said open area has a maximum width transverse to the length of said implant the maximum width of said open area being greater than the maximum height of said implant.

133. The implant of claim 115, wherein each of said openings in said top and said bottom has a central longitudinal axis and a maximum dimension transverse to the central longitudinal axis of said opening, said open area having a maximum width transverse to the length of said implant, the maximum width of said open area being greater than the maximum transverse dimension of one of said plurality of openings in one of said top and bottom.

* * * * *

UNITED STATES PATENT AND TRADEMARK OFFICE
CERTIFICATE OF CORRECTION

PATENT NO. : 7,066,961 B2  Page 1 of 1
APPLICATION NO. : 10/292539
DATED : June 27, 2006
INVENTOR(S) : Gary Karlin Michelson It is certified that error appears in the above-identified patent and that said Letters Patent is hereby corrected as shown below:

Cover Page:
Section (63), Related U.S. Application Data, line 3: change "continuation" to
      -- continuation-in-part --.
Section (56), Other Publications, page 2, line 13: change "Clinichal" to -- Clinical --.

Column 14, Line 47:
After "portion" insert -- of --.

Column 15, Line 32:
Change "portior" to -- portion --.

Column 16:
Line 34: after "portion" insert -- of --.
Line 46: change "matorial" to -- material --.

Column 17, Line 29:
After "portion" insert -- of --.

Column 18, Line 29:
Change "implant" to -- implant, --.

Signed and Sealed this

Second Day of October, 2007

JON W. DUDAS
*Director of the United States Patent and Trademark Office*